(12) United States Patent
Paul et al.

(10) Patent No.: US 10,650,823 B2
(45) Date of Patent: *May 12, 2020

(54) HEALTHCARE SYSTEMS AND METHODS USING VOICE INPUTS

(71) Applicant: CES ADVANCEMENTS, LLC, North Bethesda, MD (US)

(72) Inventors: Martin G. Paul, North Bethesda, MD (US); PV Subramanian, Frederick, MD (US)

(73) Assignee: CES Advancements, LLC, Bethesda, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 16/410,582

(22) Filed: May 13, 2019

(65) Prior Publication Data

US 2019/0279640 A1    Sep. 12, 2019

Related U.S. Application Data

(63) Continuation of application No. 16/132,134, filed on Sep. 14, 2018, now Pat. No. 10,347,255.

(Continued)

(51) Int. Cl.
| | |
|---|---|
| *G10L 15/26* | (2006.01) |
| *G16H 10/60* | (2018.01) |
| *G10L 15/07* | (2013.01) |
| *G10L 17/22* | (2013.01) |
| *G06F 3/16* | (2006.01) |

(Continued)

(52) U.S. Cl.
CPC ............ *G10L 15/265* (2013.01); *G06F 3/167* (2013.01); *G06N 20/00* (2019.01); *G10L 15/07* (2013.01);

(Continued)

(58) Field of Classification Search
CPC ......... G10L 15/22; G10L 15/26; G10L 25/66; G10L 15/02; G10L 15/1815;

(Continued)

(56) References Cited

U.S. PATENT DOCUMENTS

| | | |
|---|---|---|
| 7,010,369 B2 | 3/2006 | Borders et al. |
| 7,289,825 B2 | 10/2007 | Fors et al. |

(Continued)

OTHER PUBLICATIONS

"The robot will see you now"; Apr. 2, 2017, (published) https://www.hpe.com/us/en/insights/articles/the-robot-will-see-you-now-1708.html.

(Continued)

*Primary Examiner* — Huyen X Vo
(74) *Attorney, Agent, or Firm* — Blank Rome LLP

(57) ABSTRACT

A voice-enabled digital communications assistant powered in part using tailored machine learning models and other algorithms is used to engage with and control one or more healthcare devices or instruments such that a user is able to control the devices or instruments using natural language, conversational-like, voice commands. A command processor processes the audible instructions, while a context-aware processor monitors the present states and conditions of all devices and instruments, as well as the environment, for situational awareness purposes, including situations where executing commands may be incompatible with or conflict with the present states or conditions of devices and instruments as well as their expected future states. In addition to speech responses by the digital assistant, a separate notification engine provides audible or visual feedback to the user.

20 Claims, 6 Drawing Sheets

Related U.S. Application Data

(60) Provisional application No. 62/661,931, filed on Apr. 24, 2018, provisional application No. 62/655,555, filed on Apr. 10, 2018, provisional application No. 62/640,145, filed on Mar. 8, 2018.

(51) Int. Cl.
*G06N 20/00* (2019.01)
*G16H 40/63* (2018.01)
*G16H 40/20* (2018.01)

(52) U.S. Cl.
CPC ............. *G10L 17/22* (2013.01); *G16H 10/60* (2018.01); *G16H 40/20* (2018.01); *G16H 40/63* (2018.01)

(58) Field of Classification Search
CPC ... G10L 15/1822; G10L 15/193; G10L 25/63; G10L 15/01; G10L 15/04; G10L 15/08; G10L 15/18; G10L 15/30; G10L 17/02; G10L 17/26; G10L 19/005; G10L 2015/088; G10L 2015/223; G10L 25/51; G10L 25/90; G10L 13/043; G10L 15/16; G10L 15/20; G10L 25/78; G10L 15/265; G10L 15/28; G10L 15/32; G10L 17/04; G10L 17/06; G10L 19/26
See application file for complete search history.

(56) References Cited

U.S. PATENT DOCUMENTS

| | | |
|---|---|---|
| 9,293,141 B2 | 3/2016 | Contolini et al. |
| 2001/0032085 A1* | 10/2001 | Goedeke ............ A61N 1/37247 704/275 |
| 2008/0097176 A1 | 4/2008 | Music et al. |
| 2013/0226580 A1* | 8/2013 | Witt-Ehsani ............ G06F 3/167 704/244 |
| 2016/0253994 A1 | 9/2016 | Panchapagesan et al. |

OTHER PUBLICATIONS

"Mission-driven innovation", Sep. 29, 2017 (published) https://whatsnext.nuance.com/healthcare/artificial-intelligence-virtual-assistant-for-healthcare/.

"Special Report: AI voice assistants making an impact in healthcare", Feb. 1, 2018 (published) https://www.healthcareitnews.com/news/special-report-aI-voice-assistants-making-impact-healthcare.

"mHealth Takes a Closer Look at Digital Assistants", Mar. 14, 2017 (published) https://mhealthintelligence.com/news/mhealth-takes-a-closer-look-at-digital-assistants.

"What Will Health Care Look Like Once Smart Speakers Are Everywhere?", Mar. 7, 2018; https://hbr.org/2018/03/what-will-health-care-look-like-once-smart-speakers-are-everywhere.

* cited by examiner

HEALTHCARE SYSTEMS AND METHODS USING VOICE INPUTS

CROSS-REFERENCE TO RELATED APPLICATIONS

This is a continuation application that is based on and claims the benefit of the filing date of U.S. patent application Ser. No. 16/132,134, filed on Sep. 14, 2018, which is based on and claims the benefit of the respective filing dates of U.S. Provisional Patent Application No. 62/661,931, filed on Apr. 24, 2018; U.S. Provisional Patent Application No. 62/655,555, filed on Apr. 10, 2018; and U.S. Provisional Patent Application No. 62/640,145, filed on Mar. 8, 2018, each entitled "Healthcare Systems and Methods Using Voice Inputs." The entirety of the contents of each of the above applications is incorporated herein by reference.

BACKGROUND OF THE INVENTION

Field of Invention

The present invention relates generally to voice-assisted control of healthcare systems, including systems involving medical instruments and devices such as laparoscopic and other devices used in operating rooms.

Description of the Related Art

Voice-enabled digital communications (or conversational) assistants are available for processing audible forms of language using far field microphone technology by capturing user inputs and providing a rational response. In general, such a device might respond to "How do I change my password?" with a link to an article that sets forth the procedures a user would follow to change their password while visiting a website. Other digital assistant technology might be used to respond to a query "Are the lights on?" by outputting a verbal statement, such as, "The lights are on at 75% brightness" after interfacing with a knowledge base or sensor output that provides the light level in a particular room.

In the healthcare field, digital assistant systems have been developed with capabilities to respond to simple patient questions related to their stay in a hospital, such as queries about medications, ordering meals, and inquiring about a nurse visit. Other uses include a person asking about the wait time at an emergency room. These and other consumer-facing digital communications/conversational assistants have found only limited utility inside hospitals and other healthcare facilities.

The notion of an "Integrated Operating Room" has been sought after in the healthcare industry for some time, with the vision that such a facility would allow a surgeon and operating room staff to have easy control over all the medical systems in the facility, such as surgical devices, lighting systems, and all other intraoperative technologies. Several medical instrument manufacturers, are involved in attempts to integrate an operating room environment.

In the past, user control of operating room systems has been achieved largely through use of integrated touch panels or separate personal digital assistants (PDA; the precursor to today's smart phones and tablets). U.S. Pat. No. 7,010,369, for example, describes use of a PDA as an input/output device for wirelessly controlling a surgical table or other apparatus. Such devices require the user, for example operating room personnel, to be readily present at or access a touch panel associated with an operating room computer. This distracts that person from their many other important duties.

In other instances, user control of operating room systems has been achieved through use of microphone headsets. Such devices require a user, typically a surgeon, to control a system using a complicated series of voice-activated menus that the surgeon memorizes. In U.S. Pat. No. 7,289,825, for example, a method involving a connection between a wireless voice-enabled device and a data system using an interface for accessing the data system using voice commands spoken into a wireless headset is described. Voice commands are described as being used to facilitate data acquisition, data retrieval, order entry, dictation, audio playback, voice over IP conferencing, paging, and/or data analysis, but not for inputting instructions to medical device and instruments typically used in an operating room or the like.

Neither of the above-described approaches is particularly user-friendly, and they often involve proprietary user interfaces that control only the operating room system of a particular manufacturer. There has not been a technology platform capable of making operating room systems fully integrated in an intuitive, user-friendly manner.

Many operating room medical instruments and devices, and their associated computerized systems, as well as other operating room technologies (and technologies in a medical facility but outside the operating rooms) are connected to the facility's computer network (e.g., intranet) by wire or using a wireless protocol. Many of those system are also connectable to a wider facility network as well as the Internet (using appropriate communications and data assurance software to protect data and privacy). To ensure connectivity and communications on those networks, the instruments/devices and medical systems are addressable using an Internet Protocol (IP) address, MAC address, or other unique identification. When all of the instruments, devices, and systems in an operating room are networked in this way, there exists an opportunity to control them by one or more users using a single technology interface and platform.

With the proliferation of the Internet of Things (IoT) market of connected devices, and artificial intelligence technologies in healthcare, such as deep machine learning algorithms, systems exist for processing natural language in both written and audible forms and using that information to cause a signal to output thus performing a function or operation desired by a user.

Integrating systems in the manner suggested above would enable the unified control of all operating room equipment through a simple voice-enabled interface. The advantage of far field microphone technology coupled with artificial intelligence embodied in a digital communications assistant system is that they would enable user input of commands, instructions, comments, statements, and the like without being subject to interference from ambient operating room noise, and would allow for processing natural language instructions rather than using a menu-driven system.

Some of the challenges associated with the use of the above technology in operating room and other healthcare facilities, such as handling multiple users' voices and interfering noises, have been addressed by others. In U.S. Pat. No. 9,293,141, for example, two or more separate voice interpreting modules are used in conjunction with speech recognition algorithms, such as hidden Markov models (HMM), to interpret various operators' audio signals. Voice interpreting modules are described as interpreting speech using voice interpreting data and look-up tables of sound patterns and corresponding words. When multiple users are speaking and each is trying to send instructions to multiple devices, instruments, systems, and/or subsystems, other problems may arise, such as conflicting instructions.

Accordingly, there exists a need for a digital communications assistant-enabled system in today's healthcare industry that can integrate with and simultaneously control multiple devices, instruments, systems, and/or subsystems made by different manufacturers, handle inputs from multiple users simultaneously without conflict, and maintain awareness of the entire corpus of systems and the states of those systems to enhance the delivery of health-related services.

SUMMARY AND OBJECTS OF THE INVENTION

In one aspect of the invention, one or more far field microphones is/are positioned in the center or at some other suitable location of an operating room or other medical facility to be controlled. These interface devices may be attached to, for example, the operating room lights over a surgical field or simply hung from a cord attached to the room's drop ceiling.

In another aspect of the invention, a surgeon or other personnel in an operating room is/are able to control an array of instruments, devices, system, and subsystems using relatively simple voice commands, such as "Turn on the OR lights." Such as system might be called, by way of example only, an "AI-Suite," which is a reference to the artificial intelligence technologies used by the system that is deployed across all the rooms of a particular suite in a medical facility (e.g., the rooms of a surgical suite).

In every operating room, there are dozens of tasks and functions performed by various devices, instruments, systems, and subsystems that could readily be carried out using voice commands. These systems would include at least the following (non-limiting examples):

TABLE 1

| | |
|---|---|
| Room lights | Carbon dioxide insufflators |
| Display monitors | Electrosurgical devices |
| Digital image capture devices | Operating room tables |
| Overhead spotlights | Temperature/humidity controls |
| Laparoscopic cameras | High definition overhead cameras |
| Video streaming systems | Video conference systems |
| Printers | Video image capture devices |
| Vessel sealing devices | Coblation systems |
| Ultrasonic devices | Irrigating systems for orthopedics |
| Electrosurgical systems | Infrared illuminators |
| Robotic systems | Smoke evacuators |
| EPIC electronic medical records | Harmonic ultrasonic scalpels |
| Entertainment systems | AEM monitors |
| Telephones | Core powered instrument drivers |
| Contact lists/personnel databases | |

In another aspect of the invention, a surgeon or other medical staff is/are able to directly control the above and other instruments, devices, systems, and/or subsystems without involving other staff who would otherwise have to physically carry out a user's instructions thus reducing the efficiency of any operating room or other facility.

Some of the typical commands, instructions, comments, statements, etc., that a medical professional might use in an operating room environment to provide input to the devices, instruments, systems, and subsystems in TABLE 1 include at least the following (along with possible system responses and states/conditions) (non-limiting examples):

TABLE 2

| Command, Instruction, Comment, Statement | Responses | System States/Conditions |
|---|---|---|
| Turn room lights off/on | Okay, turning lights off/on now; Turning lights off/on; Lights are now off/on | Power to individual or multiple room lights is turned off/on or switched to an off/on position |
| Turn room lights to 85% brightness | Turning room lights to 85% The room lights are now at 85% brightness | Power to individual or multiple room light is reset to output a brightness of 85% of a maximum available setting |
| Turn Operating Room spotlight on/off | Okay, turning the spotlight on/off now; Spotlight is now on at 50%; would you like it brighter? | Power to the spotlight (or spotlights) is turned on/off and set to pre-determined initial brightness level (when turned on) of some amount less than maximum |
| Cool room to 68 degrees | Okay, the thermostat has been set to 68 degrees; the room is now at 72 degrees | The state of the analog or digital thermostat is adjusted to a requested (new) set point from its previous set point and the condition of the air quality in the room is monitored |
| Set electrocautery current to [value or setting] | Okay, the current value is now [value or setting] | The state of the current/power setting to the electrocautery instrument is adjusted to a level corresponding to the requested value or setting |
| Turn cautery on/off spray mode | Okay, the cautery spray mode is now on/off; The cautery spray is now available | Power to the spray function of the cautery device, and its ancillary devices, is set to an on/off position and the devices are placed in operating mode |
| Increase LigaSure ™ [or "vessel sealing device") settings to [value or setting] | Okay, the [Name of Instrument] setting is now [value or setting]; The device is now set to [value or setting]; The instrument setting is [X] percent higher | Power to the device is reset from a current state to a different (new) state by a step or continuous amount |

TABLE 2-continued

| Command, Instruction, Comment, Statement | Responses | System States/Conditions |
|---|---|---|
| Rotate patient 20° to the right/left | Okay, the table is being rotated now; The table is being moved to 20° angle' The table is now at a 15° rotation | Power to motors, solenoids, and sensor is turned on, or current is sent to engage the same; and the condition of the table is monitored as it rotates from its current state by the requested angle amount |
| Till patient to 20° head down/up | Okay, the table is being rotated now; The table is being moved to 20° angle' The table is now at a 15° rotation | Power to motors, solenoids, and sensor is turned on, or current is sent to engage the same; and the condition of the table is monitored as it tilts from its current state by the requested angle amount |
| Take picture | Okay; A picture [or image] has been taken and is available to be displayed; Audible shutter "click" sound | A camera device that is available and activated at the time is caused to create a digital image |
| Print picture [X] | Okay, picture ["X" or a designated image] is printing; Image is printing; Image is done printing | A printer device that is operatively connected to available camera devices is caused to print a specified image; printer may be in sleep or low power mode if not in use |
| Save picture to USB | Okay; Done; Image is saved | A computer operatively connected to available camera devices is enabled to save images using a pre-determined format (default or specified) |
| Save picture to patient chart | Okay; Done; Image is saved to patient [name] | A computer operatively connected to available camera devices and electronic health record system is updated to include a copy of the image file |
| Record video from laparoscopic camera | Okay, a video is now being recorded; Laparoscope camera is recording a video; | Power to the video camera is turned on, or if already on, then the recording function is started while monitoring storage capacity |
| Record video from HD overhead camera | Okay, a video is now being recorded; Overhead video camera is recording | Power to the video camera is turned on, or if already on, then the recording function is started while monitoring storage capacity |
| Stream video to [a website portal, website webpage, display device, room, office, other place, etc.] | Okay; The video is streaming to [identify]; An audio and video feed is now available at [identify] | Software monitoring for "True" executes a defined class or object or program that causes video source to stream play or cache playback video on a designated display or at a website webpage address |
| Send picture to [person, place, thing] | Okay; The [designated] image has been sent to [person, place, thing] | Engages a direct message or other process to transfer an image file from a storage media at one address to a designated second address |
| Share intraoperative video with Dr. [name] | Okay; The video is streaming to [identify]; An audio and video feed is now available at [identify] | Software monitoring for "True" condition executes a defined class or object or program that causes video source to stream, play, or to cache playback the designated video on a designated display or at a website webpage address |
| Display recent abdominal CT scan on [designated device, such as "monitor"] | Okay; The scan is now displayed | Software causes an image file to be displayed on a designated display device |
| What is the patient's most recent CBC lab result? | Here are the CBC results: [list] | Software accesses or issues an instruction to access the appropriate media storage device, cross-references the patient's laboratory results, and outputs the content of the results either on a display or recites the results audibly |

TABLE 2-continued

| Command, Instruction, Comment, Statement | Responses | System States/Conditions |
|---|---|---|
| Remind me to re-dose antibiotics in three hours | Okay; A reminder has been set for three hours; In one hour, re-dose antibiotics; In five minutes, re-dose antibiotics | Starts a clock timing (elapsed time) function, waits for "True" condition to occur (i.e., end of the pre-determined time period), and then outputs a reminder as an audible statement |
| Is the sponges and instrument count correct? | Yes; There are [count] sponges; There are [count] [type] [name] instruments | Computer vision and sensors monitor the disposition of various designated instruments and sponges; software causes status information to be outputted upon receiving request |
| Play classical music | Okay; Playing [name of source/station] | Causes stored or available music to play such that sound is sensible to requestor |
| Play playlist . . . | Okay; Playing [name of playlist] | Causes stored or available music to play such that sound is sensible to requestor |
| Call [name] [contact] [number] | Calling [name] [contact] [number] | Executes process to initiate a phone call to the phone number associated with the name, contact, or number |

In one aspect of the invention, a room-specific, device-specific, instrument-specific, system-specific, and/or subsystem-specific wake word, phrase, or sound could be used to preface the user's commands, instructions, comments, statements, etc., to set the digital communications assistant hardware in a state to receive a user's commands, instructions, comments, statements, etc. For example, in the case where a single digital assistant controls multiple devices, instruments, systems, or subsystems, the invocation, "<Name of Digital Assistant>, ask <invocation> . . . " can be used to identify the specific target device by using its designated name. The specific intent (request) of the user can add further information to identify the target device. If the <Name of Digital Assistant> and the <invocation> do not conclusively identify the device the user is intending to control, the digital assistant could ask the user to identify the target device. In the case where multiple digital assistants are used (such as one associated with each device, instrument, system, or subsystem), the invocation may include the identity of the specific device (or instrument, or system, or subsystem), such as, "<Name of Device>, change the <setting/condition/state> . . . ", which can be used to identify the target device.

In other medical facilities, some of the above devices, instruments, systems, and subsystems might be used, but others could be more commonly found in other situations, such as devices, instruments, systems, and subsystems used in an emergency room, pediatrics suite, radiology suite, etc. Thus, the above Table 2 is not exhaustive of the types of commands, instructions, comments, and statements, responses, and states/conditions one might expect in different facilities or areas within a hospital or other healthcare facility.

In another aspect, the voice-activated system could also be linked to the electronic medical record system (such as electronic health records (EHRs)) employed by a healthcare facility and allow viewing of laboratory studies and x-rays on operating room monitors.

In another aspect, the system would also allow a surgeon to readily control other non-medical functions in an operating room, such as selection of music, placement of telephone calls, and ordering of procedures and supplies as the need arises in real time.

Another aspect of the invention involves an algorithm that is trained on appropriate data sets to classify audible commands, instructions, comments, statements, etc. received by an input device (such as a microphone). Commands, instructions, comments, statements, etc. are of the type typically used in various rooms of a medical facility, such as those often used in an operating room, laboratory, emergency room, etc., and thus collecting those audible inputs over time can improve the accuracy of classifying them by topic (functional area), which could be useful to improve the efficiency of the entire system.

Another aspect of the invention involves a high accuracy algorithmic model that has been trained using appropriate labelled data for making rational decisions in response to a received verbal input. The model may be updated for each new system added to a medical facility so that it recognizes the semantics of terms and phrases unique to that system.

Still another aspect of the invention involves a database or knowledge base containing information for use in training the various algorithmic models in the invention, and for processing voice and other inputs. The database may include information about each individual instrument, device, system, and/or subsystem that is integrated into the overall voice-enabled control system thus described.

Another aspect of the invention is a decision support database. Such a database could include associations between inputs to the system and actions to be taken by a particular device, instrument, system or subsystem in response. For example, the semantic interpretation of a spoken invocation related to turning on a spotlight above an operating table could be associated with the system or subsystem that controls the spotlight and causes it to turn on or off. The associations, or mappings between the interpretations of voice commands and instructions for causing a device, instrument, system, or subsystem to perform a function may be incomplete and require the system to prompt the user for clarification. The decision support database could also include mappings to Evidence-Based Medicine guidelines, thereby providing the user with the ability to determine real-time optimal treatments for patients undergoing surgery. The guidelines could include National Comprehensive Cancer Network guidelines, Surgical Specialty guidelines, Cochrane databases, and third-party health-related decision systems built on machine learning models.

In one aspect of the invention, the far field microphone(s) may be connected to a local computer, a computer accessible by a facility network, or a cloud computer.

Another aspect of the invention involves a single voice-enabled digital assistant to interpret spoken phrases (speech-to-text) and then direct structured commands to the appropriate device, instrument, system, or subsystem within a particular area, such as an operating room. Such a system could be controlled using on-premise servers. Alternatively, multiple independent devices, instruments, systems, and subsystem could each have its own digital assistant, and all of them could share the same cloud-resident data model running on one or more servers.

In another aspect, an on-premises part of the system could include a cloud-connected speaker and microphone, with wake-word detection capabilities. Speech-to-text, natural language processing, intent detection, and processing, and finally text-to-speech, could all be handled in the cloud. This configuration would enable scaling, by enabling new capabilities at cloud endpoints without the need to change device hardware. Cloud-centered processing, however, introduces potential round-trip delays, but these are usually small (a few 100 milliseconds). For mission-critical applications, these small delays may not be acceptable and thus on-premises processing would be used.

For example, to address delays, certain applications of the invention could be processed on premises rather than processed through a cloud server. Also, dialog-based workflows may be implemented as one-shot or one-take to improve response time. For example, "<Name of Digital Assistant>, ask XYZ to send this picture to Dr. Smith" could be input instead of separate commands, such as "<Name of Digital Assistant>, take a picture," [response], "Send the picture to Dr. Smith," [acknowledgment response]. One-shot workflows, however, are not always intuitive or user-friendly. Thus, for certain enterprise, mission-critical applications, the on premises component of the invention may be the preferred approach. The distribution of tasks between cloud and on premises components may vary depending on the priority of various goals (i.e., round trip time, privacy, system costs, and redundancy).

Also, in cloud-based systems, privacy is a concern, thus health-related and personally-identifying data sent to the cloud may need to be encrypted and anonymized. Also, while cloud-connectivity is generally very reliable, outages may be unacceptable in many healthcare settings, such as surgical situations, so on premises capabilities may need to operate as a back-up until cloud capabilities are restored.

In another aspect, users may add their own utterances (spoken phrases) in advance of their use of a particular device, and map those utterances to a desired action (storing the mappings in, for example, a decision support database). Each user, such as a surgeon, may create his or her own profile, which can be loaded from one device to another, for example when an older model of a device is replaced or removed for service. The same profile may be portable, so the user can take it with them as they move from one facility to another.

In another aspect, a means to handle ambiguous commands, such as, "Set to level 50%," is provided. In such instances, it may be possible to infer which of the devices, instruments, systems, or subsystems the uttered command is being directed at by maintaining awareness of the current state of each device, instrument, system, or subsystem being controlled by the user along with contextual information. Some inputs for context might include the type of surgical procedure to be performed, a surgeon's head orientation and gaze, the currently active device or instrument, the device/instrument in the user's hand, and the physical location of other personnel (this could be tracked using beacons affixed to nurses, technicians, doctors, and other staff).

In still another aspect, the present system may include facial and/or voice recognition to distinguish between different speakers (obviously, due to face-covering personal protective screens, masks, and other devices, facial recognition capabilities would likely be less effective than voice recognition). The capability to identify users would enable an entire surgical team to use a single voice-enabled system, which could modify actions based on the speaker. The digital assistant could prioritize commands based on identified speakers such that commands by Speaker A might take priority over commands by Speaker B if they conflict.

In another aspect, a type of "access control" is used so only a particular user can issue certain commands. This could be implemented during a user login procedure at an input device prior to the user entering a room or facility that has been configured with the present invention. For example, the user may be required to enter an identification or authorization code using a wall-mounted touchpad outside the room or facility. The user could instead be required to swipe in a card reader an identification card equipped with a magnetic stripe containing identifying information. Alternatively, the user may be required to provide real-time biometric identification information, such as presenting a fingerprint or voice pattern. Or, the user may be automatically (passively) recognizing within the room/facility by face or voice recognition, or from interrogating an RFID chip attached to the user or by receiving a signal from a beacon attached to each user.

Another aspect provides for a notification engine for asynchronous notifications or interactions. The notification engine of the voice-enable digital communications assistant system may determine that an action should be taken (based on the state or condition of one or more devices, instruments, systems, or subsystems and the context at any given time) and outputs a sound or displays an indicia to inform the user (or users) that it has a notification. The user would then ask the digital assistant to read these out to the user.

For example, in a surgical environment, there may be a process that takes several minutes for an instrument to reach a particular temperature. The digital assistant would monitor the state (temperature) of the instrument and cause a notification engine to output a sound or display an indicia to let the user know that it has a notification that the instrument is ready (or it may simply output audible speech to notify the user). This aspect of the invention would be supported by a context engine, which includes one or more context-aware algorithms to ensure that the notification is delivered at the right time, without interrupting an ongoing dialog. Notification could be delivered to some locations/personnel, and not broadcast across all speakers.

In one aspect, a voice-enabled digital communications assistant may be embedded in a smart device, instrument, system, or subsystem. Alternatively, a device, instrument, system, or subsystem without voice-input features could be upgraded by use of an add-on "adapter," whereby a voice-input device is connected to the equipment and directly and exclusively piped to a speaker output of a digital assistant. Voice processing software would then convert spoken phrases to the specific menu-driven vocabulary of the equipment.

DETAILED DESCRIPTION OF THE INVENTION

Figure 1:
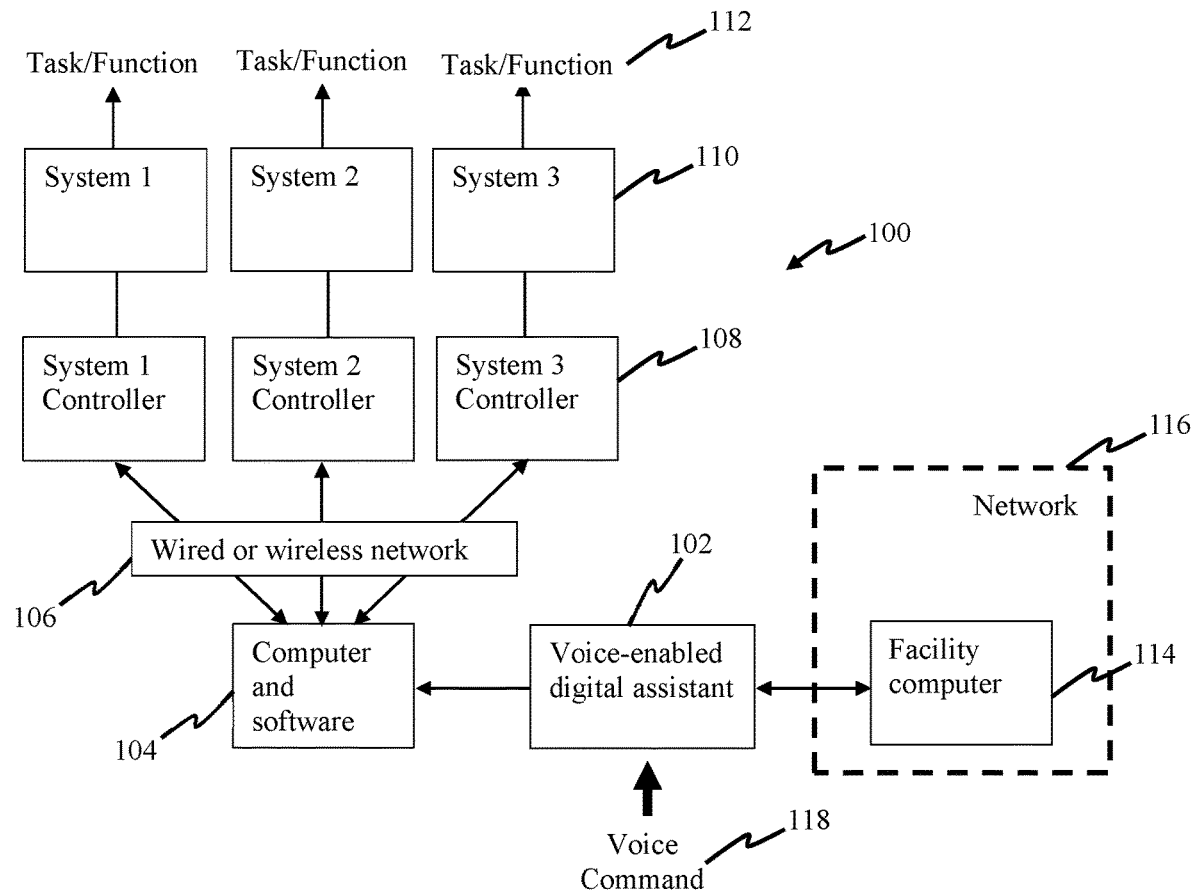
FIG. 1 is a simplified schematic block diagram of some of the components of a voice-enabled digital assistant system used in a medical or other facility.

One or more embodiments of the present invention are described for illustrative purposes, it being understood that the invention may be embodied in other forms not specifically shown in the drawings and/or described. The figures illustrating aspects of the invention will be described with respect to the structure and functions that achieve one or more of the objects of the invention and/or receive the benefits derived from the advantages of the invention.

In the proceeding and following descriptions, the terms "device," "instrument," "system," and "subsystem" refer to hardware and software that could be used in connection with the present invention. Those terms are not intended to be limiting, and are not exclusive category labels. For example, a device might be considered an instrument, and vice-versa. A system could refer to one or more device or instruments along with associated software. A subsystem could refer to a portion of a larger system, but a subsystem itself could be perceived as its own system.

Turning now to FIG. 1, a simplified schematic block diagram of some of the components of a voice-enabled digital assistant system 100 used in a medical or other facility is depicted. The system 100 includes a voice-enabled digital assistant subsystem 102 connected to one or more computers (and associated software) 104, a network 106, and one or more system controllers 108 corresponding to one or more systems 110 that perform a particular task or function 112. The voice-enabled digital assistant subsystem 102 is also connected to a facility computer system 114 via a facility network 116.

The voice-enabled digital assistant 102 in FIG. 1 includes a far field microphone (not shown) for receiving natural language voice commands 118 as its percepts. Using machine learning models that have been trained and tested on a suitably large corpus of data (e.g., voice recordings), the microphone's processor monitors for voice commands, instructions, comments, statements, etc., and then the models interpret the same using natural language processing or other machine learning algorithms. The digital assistant software associated with the voice-enabled digital assistant 102 then makes a rational output to the computer 104.

The one or more computers/software 104 (only one computer/software 104 is shown in FIG. 1 for simplicity) includes one or more processors and processor-enabled media storing software for executing by the processors one or more software applications or modules as needed. The network 106 may be a wireless or wired network, such as a local area network or wide area network, and it may be dedicated to the system 100.

The systems 110 that are controlled by voice are represented by "System 1," "System 2," and "System 3," but any number of systems could be included. Each system represents a medical instrument, device, or system of instruments or devices located in a medical or other facility. For example, "System 1" could be a bank of operating room lights and their associated software.

Each of the systems 110 is associated with a system controller 108, which causes the system 110 to perform a function, task, operation, or otherwise changes the state of the system. For example, if "System 2" represents a lavage system, "System 2 Controller" would encompass the combination of pumps, valves, microcontrollers, etc. (not shown), that are provided with the lavage system by its respective manufacturer or added later by a purchaser or user.

Each of the system controllers 108 is connected to the one or more computers and associated software 104. The software running on the computer 104 outputs instructions to, and monitors the state of, each of the systems 110/system controllers 108. For example, the computer 104 may output an instruction to the "System 3 Controller" associated with "System 3," which in this example may be an operating room table, to tilt the table to a specific angle. A feedback loop (as best shown in FIG. 2) provides state information to the computer/software 104 so that it knows the table's current tilt angle and updates that information once the new angle is achieved.

The facility's computer 114 could store or access one or more user profiles, such as a surgeon's profile. Each user may create his or her own profile, which can be loaded from one device to another, for example when an older model of a system 110 device or instrument is replaced or removed for service. The same user profile may be portable, so the user can take it with them as they move from one facility to another (e.g., when they move from a hospital setting to the user's normal practice office setting). The user profile may include such information as a user's identity, biometric information for identifying and authenticating the user, default parameters for one or more systems 110 (e.g., default settings for lighting, music selection, table height, instrument states, etc.), user's and other's email address, access codes to access electronic health record systems, preferred guidelines for specific procedures, commonly-used phone numbers, patient information, and other information.

Figure 2:
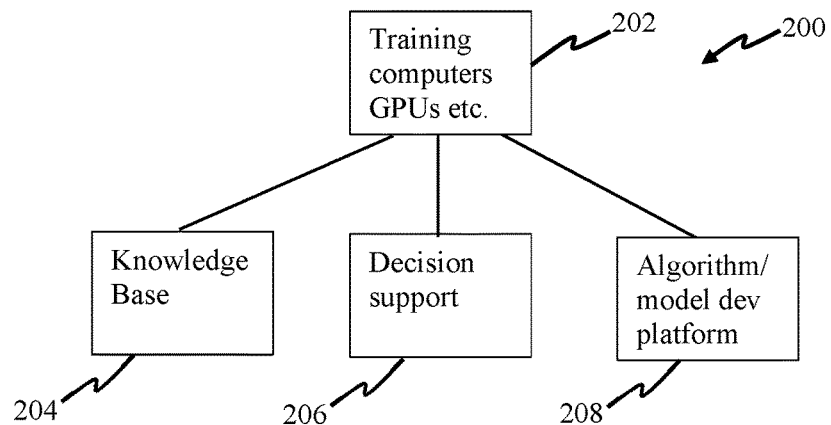
FIG. 2 is a simplified schematic block diagram of a system for developing algorithmic models used by the digital assistants of FIG. 1.

Turning now to FIG. 2, shown therein is a simplified schematic block diagram of a system 200 for developing algorithmic models used by the digital assistants of FIG. 1 and for providing information for a knowledge base and decision support database. To enable the integrated system to operate, a separate training and testing computer or computers 202 with appropriate and sufficient processing units/cores, such as graphical processing units (GPU), are used in conjunction with a knowledge base 204 (for example, typical operating room commands and their associated semantic/linguistic meanings), a decision support matrix 206 (for example, cross-referencing possible algorithmic decisions, system states, and third-party guidelines), and an algorithm (model) development module 208 (for example, a platform of available machine learning algorithms for testing with data sets to identify which produces a model with accurate decisions for a particular instrument, device, or subsystem).

The process for training and testing voice-enabled algorithms is well known in the art, but new discoveries are being made on a regular basis. It is understood that future technologies for controlling systems or a system of systems using voice commands, instructions, comments, statements, etc. can be used with the present invention.

Figure 3:
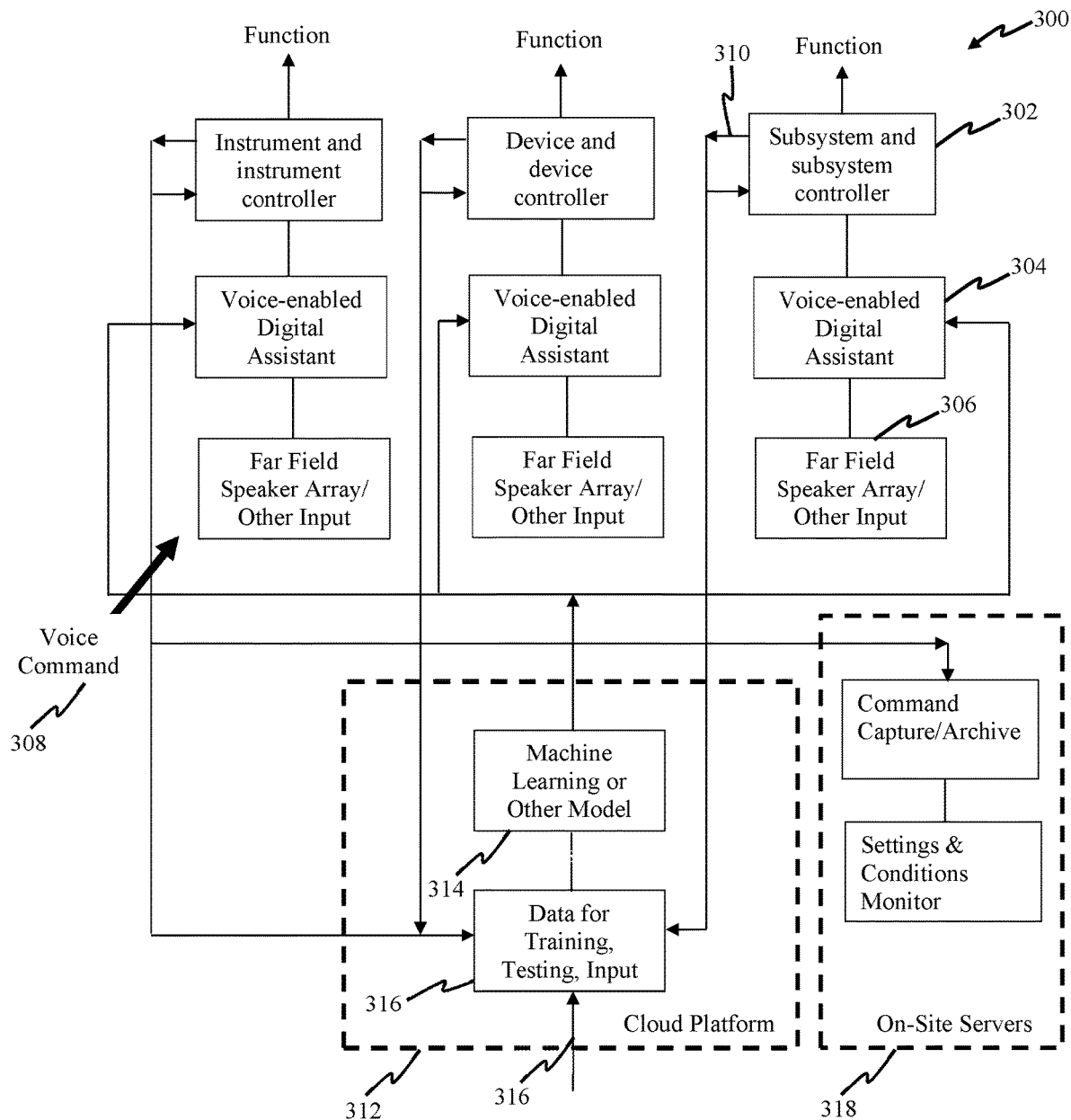
FIG. 3 is a simplified schematic block diagram of some of the components of another voice-enabled digital assistant system used in a medical or other facility.

Turning now to FIG. 3, shown therein is a simplified schematic block diagram of some of the components of another voice-enabled digital assistant system 300 for used in a medical or other facility. In this figure, an individual or discrete device, instrument, system, or subsystem 302 is equipped with a corresponding digital assistant 304, which itself is operatively connected to a far field microphone device 306 for receiving a commands, instructions, comments, statements, etc. 308 from a user of the device, instrument, system, or subsystem. The user may be, for example, a medical professional such as a surgeon engaged in an operation within an operating room facility. The digital assistant 304 thus augments the user's operation of the device, instrument, system, or subsystem 302 by receiving the audible commands, instructions, comments, statements, etc., processing the same using an algorithmic model for that particular device, instrument, system, or subsystem 302, and outputting a signal to the same that the digital assistant 304 is associated with. The outputted signal causes the device, instrument, system or subsystem 302 to take an action, perform a task, or perform a function corresponding to the user's commands, instructions, comments, statements, etc.

Each device, instrument, system, or subsystem 302 includes a controller that includes the above-mentioned algorithm that operates the hardware aspects of the device, instrument, system, or subsystem 302.

The controller includes a feedback loop 310 that continuously monitors the state or condition of the device, instrument, system, or subsystem 302, and also provides that state and condition information to a cloud-based platform 312 (which could instead be on-site) that updates algorithmic models 314 for the device, instrument, system, or subsystem, and sends the updated models to the digital assistant 304 associated with the device, instrument, system, or subsystem. That way, the digital assistant 304 is constantly learning with new data 316 from the system 300 and from third-party sources and is able to improve its accuracy (with caution not to over-fit the model) in responding to the user's commands, instructions, comments, statements, etc. 308 and outputting appropriate signals to the controllers 302.

Figure 8:
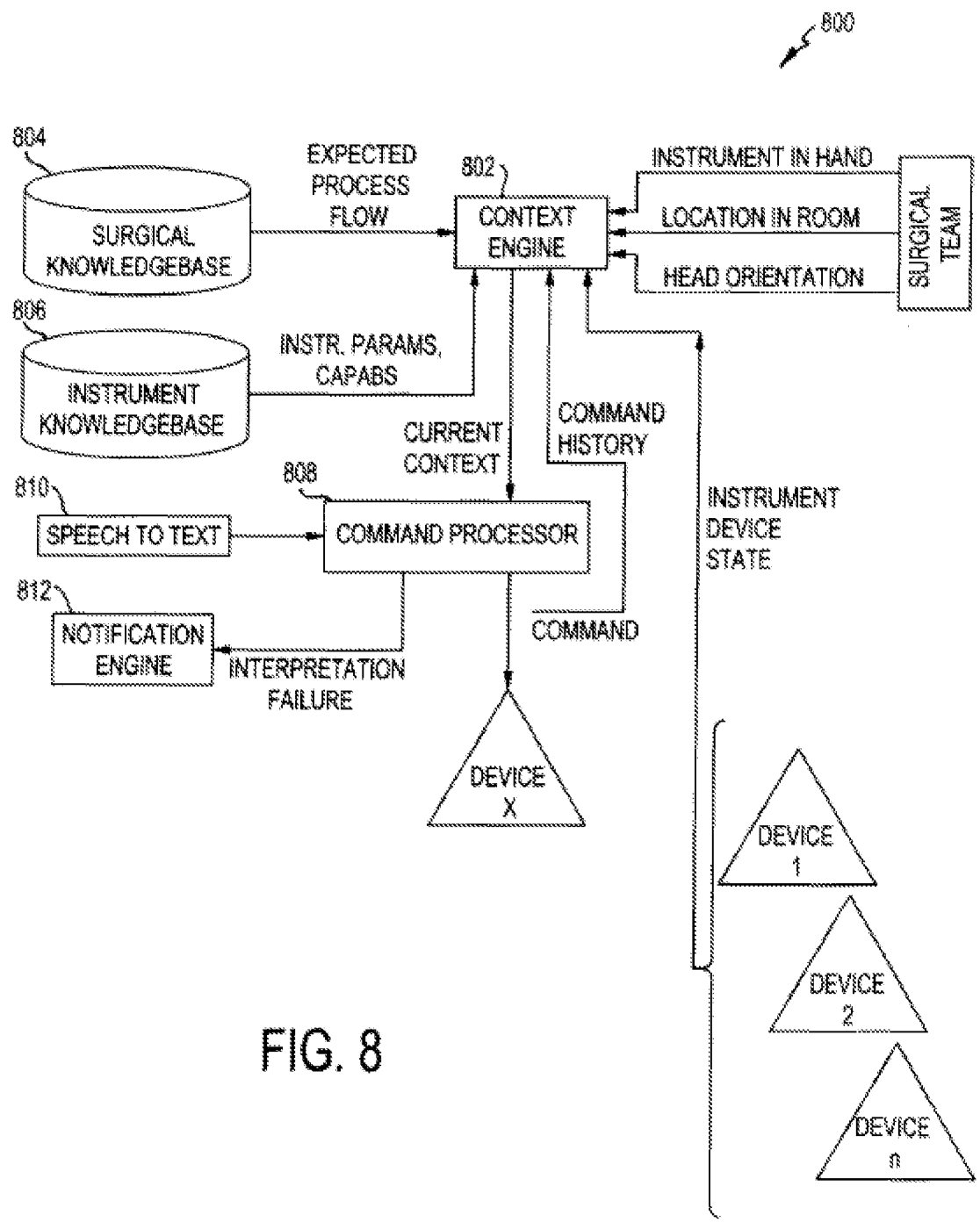
FIG. 8 is another simplified schematic block diagram of some of the components of another voice-enabled digital assistant system used in a medical or other facility.

Moreover, the feedback loop 310 provides for asynchronous notifications or interactions with the user(s). That is, the controller 302 may output an instruction to a notification engine (as shown in FIG. 8) to output a sound or display an indicia using an output device (not shown) to inform the user(s) that it has a notification. The user would then ask the digital assistant 304 to read these out to the user(s), which the notification engine would provide.

The user's commands, instructions, comments, statements, etc., and the state and condition information from each device, instrument, system, or subsystem 302 are also captured and archived in one or more on-site networked computers 318 (which may be designated data storage devices or application servers) located at the facility for other uses and purposes, such as training, compliance, insurance, and record-keeping purposes. The one or more computers 318 may store and archive a history or log of settings and condition states for each instrument, device, system, or subsystem for the same uses and purposes.

Figure 4:
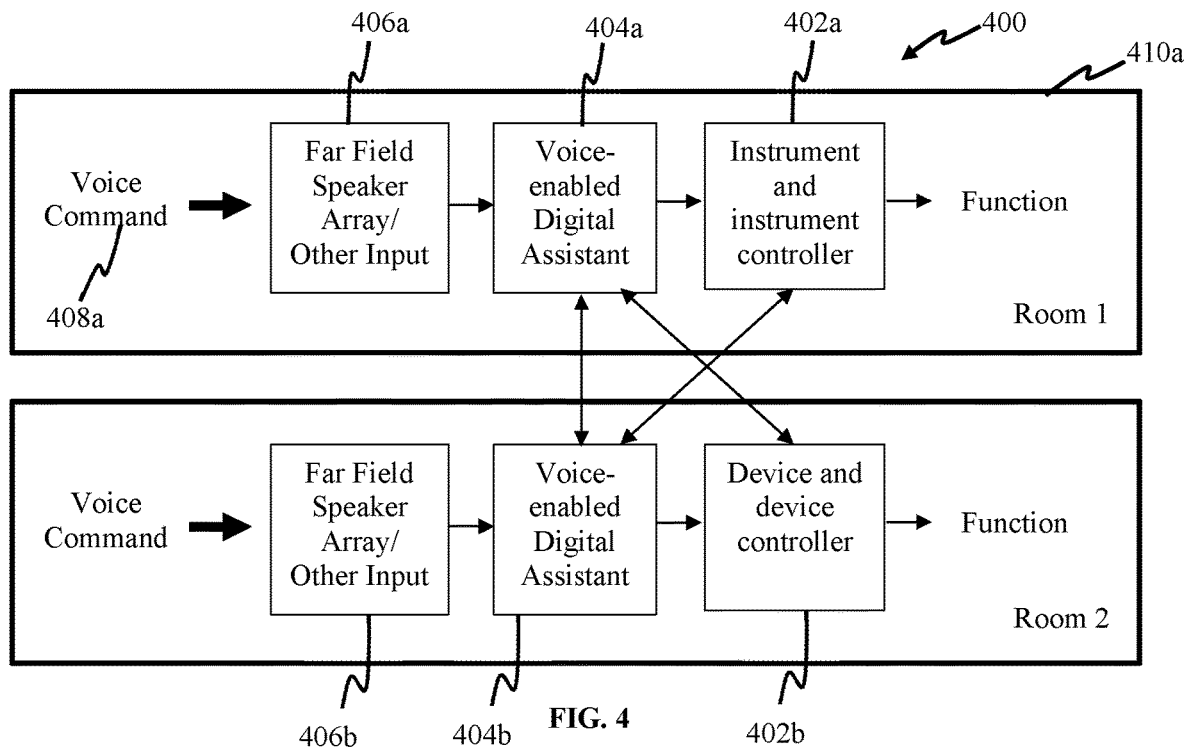
FIG. 4 is a simplified schematic block diagram of some of the components of yet another voice-enabled digital assistant system used in a medical or other facility.

Turning now to FIG. 4, shown therein is a simplified schematic block diagram of some of the components of yet another voice-enabled digital assistant system 400 for used in a medical or other facility. In this figure, the same voice-enabled digital assistant 402a and far-field speaker array 404a technology described previously is shown being used in different rooms of a medical facility.

Room 408a ("Room 1") could be, for example, an operating room of an operating room suite in a hospital. "Room 2" could be, for example, a different operating room of the same operating room suit of the hospital. A user in Room 1 could issue a voice command 408a in that room intended to cause a device or instrument 402a in Room 1 to perform a function, or intended to cause a device or instrument 402b in Room 2 to perform a function.

Figure 5:
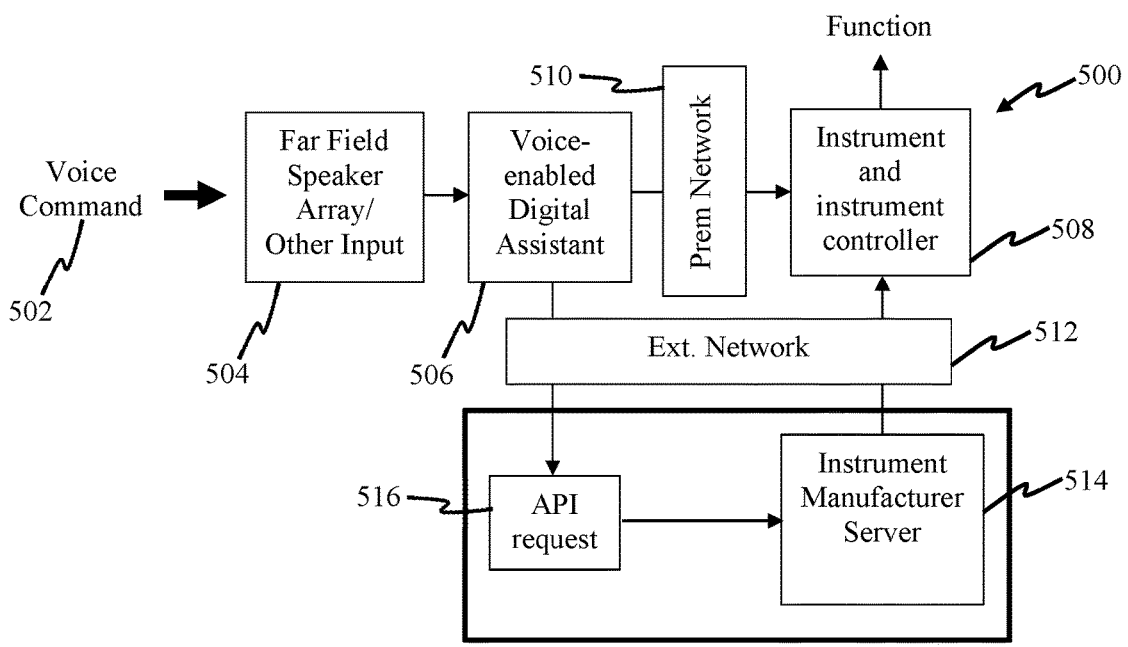
FIG. 5 is a simplified schematic block diagram of some of the components of another voice-enabled digital assistant system used in a medical or other facility.

Turning now to FIG. 5, shown therein is a simplified schematic block diagram of some of the components of another voice-enabled digital assistant system 500 for used in a medical or other facility. As shown, a user's commands, instructions, comments, statements, etc. 502, are received by a far-field microphone, array of microphones, or other voice input device 504, which are then processed by a digital communications assistant 506, which may be integral to a specific medical facility room (or specific location, space, or area within the medical facility), or may be integral to and associated with a particular one or group of instruments, devices, or subsystems.

The digital assistant 506 may be directly operatively connected to the one or more instruments, devices, systems, or subsystem 508, or, in the example shown, it may be connected via the facility's on-premise network 510 (e.g., a local area network, or intranet), or via a wireless protocol such as Bluetooth®. In such a configuration, the digital assistant 506 may cause a signal to be outputted to the one or more instruments, devices, system, or subsystems containing information for causing the instruments, devices, system, or subsystems to perform some function, operation, or otherwise change its state from a current state to a different state (e.g., turn on, turn off, etc.).

Alternatively, the digital assistant 506 may be connected or connectable to an external network 512, such as the Internet, to send a request to a remote server 514. The request may be, for example, an application programming interface (API) request 516, sent over the Internet 512 to the respective manufacturer of the one or more instruments, devices, systems, or subsystems 508. The API request 516 could instead be sent to a service provider (such as a cloud service provider; not shown) that provides data center server services on behalf of the manufacturer.

The manufacturer's (or its service provider's) dedicated or cloud server is provided to receive API requests 516 from multiple digital assistants 506 at multiple medical facilities. It processes the API request 516 and outputs a signal via the Internet 512 in response. The signal contains information for causing the one or more instruments, devices, system, or subsystems 508 to perform some function, operation, or otherwise change its state from a current state to a different state (e.g., turn on, turn off, etc.).

Figure 6:
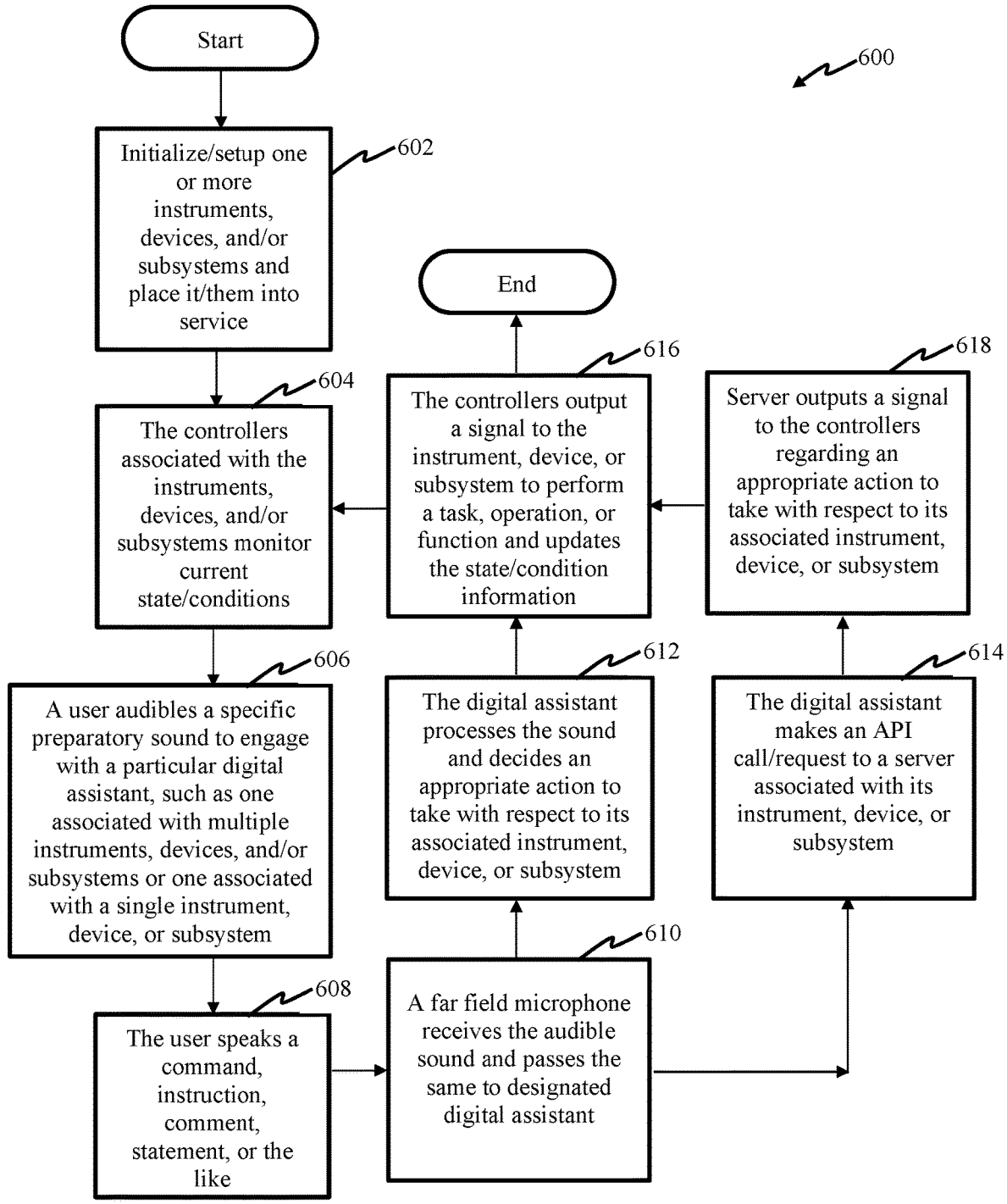
FIG. 6 is a process flow diagram according to a voice-enabled digital assistant system used in a medical or other facility.

Turning now to FIG. 6, shown therein is a process flow diagram according to a voice-enabled digital assistant system 600 used in a medical or other facility. In a first step 602, one or more instruments, devices, systems, and/or subsystems is/are initialized or setup within the facility's digital assistant system and placed into service.

In a next step 604, the controllers associated with the instruments, devices, systems, and/or subsystems monitor a current state or condition of the instruments, devices, system, and/or subsystems.

In the next step 606, a user makes an audible preparatory sound to engage with a particular digital assistant, such as one associated with multiple instruments, devices, systems, and/or subsystems or one associated with a single instrument, device, system, or subsystem. The audible sound may be one that places the digital assistant in a state to receive further audible information.

In the next step 608, the user speaks a command, instruction, comment, statement, or the like.

In the next step 610, a far-field microphone receives the audible sound associated with the command, instruction, comment, statement, or the like, and passes (processes) the same to the designated digital assistant application. The context awareness system as previously described and further described below acts as the gatekeeper for processing the sound to the appropriate digital assistant application.

In the next step 612, the digital assistant processes the sound and decides an appropriate action to take with respect to the associated instrument, device, or subsystem, and outputs a signal to that instrument's, device's, system's or subsystem's controller. Alternatively, in step 614, the digital assistant makes an API call/request to a server associated with its instrument, device, system, or subsystem.

In the next step 616, the controllers output a signal to the instrument, device, system, or subsystem to perform a task, operation, or function. Alternatively, in step 618, a server associated with the instrument, device, system, or subsystem outputs a signal to the controllers regarding an appropriate task, operation, or function to take with respect to its associated instrument, device, system, or subsystem.

In the next step 604, which now becomes a feedback loop, the controllers update the state/condition information associated with their respective instrument, device, system, or subsystem and monitors that state/condition until a new signal is received.

Figure 7:
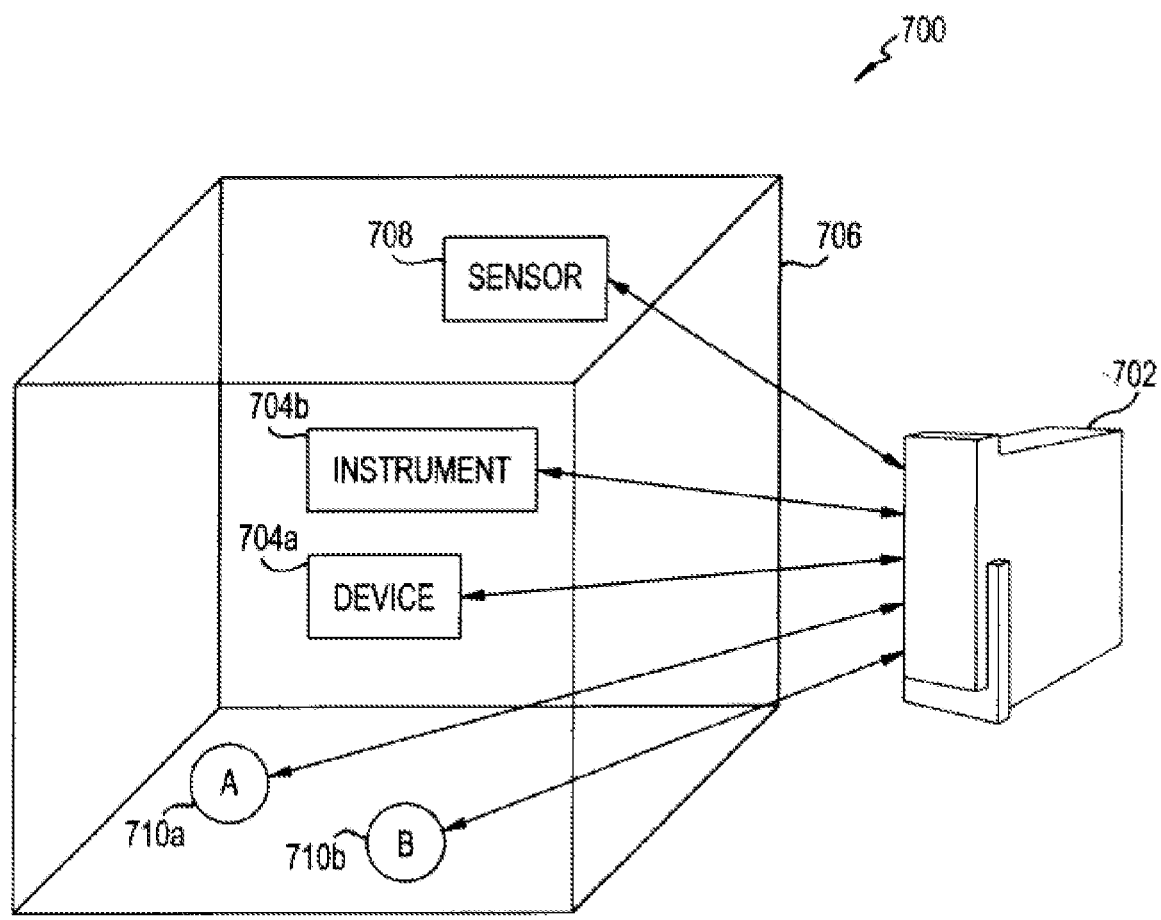
FIG. 7 is a simplified schematic block diagram of some of the components of another voice-enabled digital assistant system used in a medical or other facility.

Turning now to FIG. 7, shown therein is a simplified schematic block diagram of some of the components of another voice-enabled digital assistant system 700 used in a medical or other facility. In particular, the digital assistant software may reside on one more on-premise servers 702 and used to interface with one or more devices 704a and instruments 704b. In the configuration shown, a room 706, such as an operating room of a hospital, may have one or more devices 704a and instruments 704b, sensors 708, and beacons 710a, 710b, attached to individuals present in the room 706.

With regard to each of the devices, instruments, systems, and subsystems in the room 706, each may involve several signals that are monitored, such as those for temperature, voltage, revolutions per minute, dosage rates, held by (i.e., which user), location in the room 706, orientation (where relevant), and others. For each person in the room 706, each may be monitored for their location (via beacons 710a, 710b), function/role, head orientation, eye gaze, microphone input, and hand contents. The room 706 itself may be monitored for temperature, humidity, illumination/brightness, ventilation, pressure, door status, and other states and conditions.

Turning now to FIG. 8, which is a block flow diagram of another voice-enabled digital conversational assistant system 800, shown therein is the previously-mentioned context engine 802, a knowledge base 804 (in this example, a "surgical" knowledge base), a device/instrument/system/subsystem knowledge base 806, a command/instruction/comment/statement processor 808, a speech-to-text model module 810, a notification engine 812, and devices designated "Device 1", "Device 2," . . . , "Device n" and "Device x" (which may be instruments, systems, or subsystems by designation).

The digital assistant software includes a context engine 802, which include algorithms (not shown) running on the server 702 that are dedicated to monitoring the various states and conditions of multiple persons and equipment in the room to provide context to the decision algorithms that process speech commands from the users. The context engine 802 helps resolve ambiguous invocations uttered by the users by understanding the context in which commands are made, and, if unresolvable, outputs a request for clarification from the user. Within an operating room, the context engine 802 is a computing system that takes in a number of real-time inputs relating to the surgical process underway, to develop a digital awareness of the current state. The current state, as well as anticipated next steps, can then be used to improve command interpretation.

The notification engine 812, which may be a software program running on-premise or in-cloud, is responsible for delivering notifications to the user and others present in the room. The notification engine 812 also uses the context engine 802 to determine when and how notifications are delivered. For example, the notification related to an instrument reaching a specific temperature may not be critical, and can be delivered during a pause in a surgical process. It may even be delivered only to a particular person designated to receive certain notifications (e.g., the head surgical nurse). On the other hand, if the instrument is not behaving as expected, the system may need to alert the entire room right away.

Additionally, notifications may be delivered through room audiovisual units, or into headsets/head-mounted units of specific personnel. This decision can also be made by the notification engine 812, based on the nature of the notification and current state of the environment.

If a user is performing a particular procedure that involves Device x that is operating at some condition state at time t and the user issues a voice command to alter the condition of a variable that would negatively affect the procedure but positively alter a different device (e.g., Device 1, Device 2, . . . , Device n) located in the room 706, the context aware algorithms of the context engine 802 would understand that the user's instruction was meant for the Device x and not the other devices.

For example, if a user speaks the instruction, "Record video," the system might interpret this to mean 1) record, using an overhead camera, during an open procedure, or 2) record, using a laparoscopic camera, during a laparoscopic procedure. Here, the system would know the state of the environment within the operating room and conclude that a laparoscopic procedure is being performed because an insufflator and light source are also operating at the time, and thus it would select option 2) and cause the laparoscopic camera to begin recording (or turn on first, if the state of the camera is determined to be turned off).

In another example, if a user speaks "Turn laparoscopic light source on," the system would power on the light source if the camera is connected and turned on. If the camera is not on, the notification engine 812 would receive a signal from the command processor 808 to output a notification to "Turn on camera before turning on light source." This could help prevent patient burns from the light source being turned on prematurely or for an unnecessary amount of time.

In both of the above examples, an action based on knowledge of the present state of the environment (i.e., the state of every device, instrument, system, or subsystem, e.g., Device 1, Device 2, . . . , Device n), a form of situational awareness, may be implemented using knowledge bases 804, 806 and a decision support algorithms of the context engine 802. The knowledge bases 804, 806 or the context engine 802 could store decision trees such as: given Command X (at time t), if condition A exists, and if condition B exists, and if condition C exists, then take action D; but if condition A, B, and E exist, then take action F).

The same context awareness feature of the context engine 802 can also be used in the case of multiple users. For example, when two users (e.g., a surgeon and an anesthesiologist or some other individual in an operating room) give separate verbal commands (or just one person gives two separate commands) the system interprets them in the context of what is going on at a particular moment (i.e., the observed state of the environment) so that it can properly implement the commands. By themselves, each command might cause a device or instrument to perform either Function 1 or Function 2 if each command is considered independently and in isolation, but might cause a device or instrument to perform Function 3 when the system takes into context all that is happening at the time (or it at least prompts the user for clarification before performing Function 3). The latter approach involves a system that has an overall awareness of what is happening so that it can make the optimal or best rational decisions.

By way of further example, if the spoken command is "set to temperature level 6," and the only instrument with temperature setting capability is presently in the surgeon's hand, it is very likely that it is the instrument at which the command is directed. If the instrument's capabilities database indicates that it supports setting by "levels," that is further reinforcement that the command is directed to the instrument and not to some other device, instrument, system, or subsystem. Moreover, if the surgical knowledge base 804 associated with the procedure indicates that in a few minutes from time t, (i.e. the current state of the process), a high temperature instrument will likely be used, the command has a high likelihood of being relevant to the instrument the surgeon is using.

The context engine 802 receives dynamic real-time inputs from sensors attached to head-mounted displays (e.g. location and orientation), device, instruments, systems, subsystems, staff ID badges, as well as digitally represented states of smart lights, surgical devices, etc. The context engine 802 may provide the command processor 808 a number of ranked options. The context engine 802 may be powered by machine learning models, such as the aforementioned decision trees as well as Markov chains or other suitable algorithms.

Although certain presently preferred embodiments of the disclosed invention have been specifically described herein, it will be apparent to those skilled in the art to which the invention pertains that variations and modifications of the various embodiments shown and described herein may be made without departing from the spirit and scope of the invention. For example, while far field microphone devices are described, a single microphone in proximity to the user, such as one clipped to the user's clothes, could be used. Accordingly, it is intended that the invention be limited only to the extent required by the appended claims and the applicable rules of law.

We claim:

1. A system comprising:
an audio input device for receiving sound in a space;
a knowledge base containing records tangibly stored on one or more media devices, the knowledge base containing information about one or more capabilities of a device or instrument and at least one medical procedure workflow that involves the use of the device or instrument;
a processor for receiving at least one electronic signal comprising information about a state of the device or instrument and for outputting a signal containing information about a state of a medical procedure; and
a processor-executable software stored on one or more second media devices adapted for,
when the sound comprises a spoken utterance, extracting from the sound a semantic meaning using a machine learning technique,
selecting between a new state or a current state for the device or instrument based on the semantic meaning, the current state, the information about the state of the medical procedure, and the capabilities information, and
if a new state is selected, generating a control signal to send to the device or instrument for causing the device or instrument to alter to the new state.

2. The system of claim 1, wherein the device or medical instrument is selected from the group consisting of a room light, a display monitor, a still image camera, a spotlight, a laparoscope, a video image camera, a computer for streaming video, a printer, a bodily vessel sealer, an ultrasonic imager, an electrosurgical apparatus, a robotic apparatus, an EPIC electronic medical record, an entertainment apparatus, a telephone, a contact lists/personnel database, a carbon dioxide insufflator, an operating room table, a temperature control apparatus, a humidity control apparatus, an overhead surgical table monitoring camera, a video conference apparatus, a coblation apparatus, an orthopedic irrigator, an infrared illuminator, a smoke evacuator, a harmonic ultrasonic scalpel, an AEM monitor, a core powered instrument driver, a thermostat, an electrocauterizer, a clock or timing apparatus, and a computer vision-based medical items tracking apparatus.

3. The system of claim 1, wherein the medical procedure workflow identifies at least one step for performing the medical procedure.

4. The system of claim 1, wherein the knowledge base information further includes information about one or more performable functions of the device or instrument.

5. The system of claim 1, wherein the audio input device is a far-field microphone, and wherein the space is one or more rooms in a facility for performing the medical procedure.

6. The system of claim 1, wherein the processor is part of an on-premises computer at a medical facility, and wherein the processor-executable software is part of one or more dedicated cloud-based servers different than the on-premises computer.

7. The system of claim 1, wherein the processor-executable software is further adapted to selecting one of a new state for the device, a current state for the device, or a notification to be sent to a notification device, based on the semantic meaning, the current state, the information about the state of the medical procedure, and the capabilities information.

8. The system of claim 1, wherein the processor-executable software is further adapted to receiving from the audio input device a signal containing information representing the spoken utterance.

9. The system of claim 8, wherein the received signal is received via an application programming interface.

10. The system of claim 1, wherein the one or more media devices containing the knowledge base, and the one or more second media devices containing the software, are part of the same device or instrument.

11. The system of claim 1, further comprising a notification device for outputting a sound or indicia upon receipt of information indicative of the device or instrument being in the new state.

12. The system of claim 1, further comprising a beacon attachable to a person for outputting a signal in the space useful in differentiating a spoken utterance by the person from the sound in the space received by the audio input device.

13. The system of claim 1, wherein the audio input device and the device or instrument are co-located in the space.

14. A medical device or instrument comprising:
at least one component characterized by one or more capabilities that define one or more functions the at least one component can perform;
a memory device storing information about the one or more capabilities and a workflow that includes the one or more defined functions and further storing information about at least one step of a medical procedure that involves the one or more functions;
an audio input device for receiving sound in a space, differentiating a spoken utterance from the sound; and outputting a signal containing information representing the spoken utterance; and
a software stored on a media device and executable by a processor for,
extracting semantic meaning from the spoken utterance by processing the information in the output signal using a machine learning technique,
selecting from the information in the memory device a function from the one or more functions for the component to perform based on the extracted meaning, a present state of the device or instrument, and the workflow, and
generating a control signal for sending to the at least one component that includes information useful for causing the component to perform the selected function.

15. The medical device or instrument of claim 14, wherein selecting the function is further based on identifying if the device or instrument is in a current state of use, if the medical procedure has begun, and if the device or instrument is identified in the workflow as needed to perform the at least one step of the medical procedure.

16. The medical device or instrument of claim 14, wherein the device or medical instrument is selected from the group consisting of a room light, a display monitor, a still image camera, a spotlight, a laparoscope, a video image camera, a computer for streaming video, a printer, a bodily vessel sealer, an ultrasonic imager, an electrosurgical apparatus, a robotic apparatus, an EPIC electronic medical record, an entertainment apparatus, a telephone, a contact lists/personnel database, a carbon dioxide insufflator, an operating room table, a temperature control apparatus, a humidity control apparatus, an overhead surgical table monitoring camera, a video conference apparatus, a coblation apparatus, an orthopedic irrigator, an infrared illuminator, a smoke evacuator, a harmonic ultrasonic scalpel, an AEM monitor, a core powered instrument driver, a thermostat, an electrocauterizer, a clock or timing apparatus, and a computer vision-based medical items tracking apparatus.

17. The medical device or instrument of claim 14, wherein the state is characterized by one or more of being turned on, being turned off, being in a lower than maximum power mode, a level of illumination brightness, a temperature set point, an electrical current amount, a fluid flow rate amount, a graduated setting value, an electronic indication associated with a true value, an electronic indication associated with a false value, an angle relative to horizontal, a rotation angle relative to a nominal angle, an image data being stored in a memory device, a level of audible sound, an amount of data stored in a memory, and a universal resource locator of a displayed website.

18. A method comprising:
receiving in an audio input device a real-time sound in a space and outputting a signal containing information representing the sound;
differentiating a spoken utterance sound from the output signal by processing the output signal through an algorithm that converts sound to text;
identifying from the output signal whether the spoken utterance includes a word or phrase corresponding to a device or instrument by comparing the spoken word or phrase to a predetermined list of words or phrases;
extracting from the spoken utterance a semantic meaning using a machine learning technique;
selecting from a knowledge base tangibly stored on one or more media devices a new state or a current state for the device or instrument based on the semantic meaning, the current state of the device or instrument, an information about the capabilities of the device or instrument, and at least one medical procedure workflow that involves the use of the device or instrument; and
if the new state is selected, generating a control signal to send to the device or instrument for causing the device or instrument to alter to a new state, or,
if the current state is selected, generating a notification signal to send to a notification device.

19. The method of claim 18, wherein the device or medical instrument is selected from the group consisting of a room light, a display monitor, a still image camera, a spotlight, a laparoscope, a video image camera, a computer for streaming video, a printer, a bodily vessel sealer, an ultrasonic imager, an electrosurgical apparatus, a robotic apparatus, an EPIC electronic medical record, an entertainment apparatus, a telephone, a contact lists/personnel database, a carbon dioxide insufflator, an operating room table, a temperature control apparatus, a humidity control apparatus, an overhead surgical table monitoring camera, a video conference apparatus, a coblation apparatus, an orthopedic irrigator, an infrared illuminator, a smoke evacuator, a harmonic ultrasonic scalpel, an AEM monitor, a core powered instrument driver, a thermostat, an electrocauterizer, a clock or timing apparatus, and a computer vision-based medical items tracking apparatus.

20. The method of claim 18, wherein the step of differentiating a spoken utterance sound from the output signal includes differentiating a spoken utterance sound made by a first person from a spoken utterance sound made by a second person.

* * * * *